United States Patent [19]

Alam

[11] Patent Number: 5,990,134
[45] Date of Patent: Nov. 23, 1999

[54] ORAL DROPERIDOL COMPOSITIONS AND METHOD FOR TREATING MIGRAINE

[75] Inventor: Abu Alam, Lake Forest, Ill.

[73] Assignee: Taylor Pharmaceuticals, Buffalo Grove, Ill.

[21] Appl. No.: 09/133,106

[22] Filed: Aug. 12, 1998

[51] Int. Cl.⁶ .................................................. A61K 31/44
[52] U.S. Cl. ........................................................ 514/338
[58] Field of Search ............................................. 514/338

[56] References Cited

U.S. PATENT DOCUMENTS

| | | | |
|---|---|---|---|
| 5,118,508 | 6/1992 | Kikuchi et al. | 424/448 |
| 5,288,497 | 2/1994 | Stanley et al. | 424/440 |
| 5,310,561 | 5/1994 | Jao et al. | 424/465 |

OTHER PUBLICATIONS

Wang, et al. Droperidol Treatment of Status Migrainosus and Refractory Migraine, Headache. Jun., 1997, pp. 377–382.

Wang, et al., Droperidol Treatment of Acute Refractory Migraine and Status Migrainosus, Headache, Apr., 1996, p. 280.

John F. Rothrock, MD., Treatment of Acute Migraine with Intravenous Droperidol, Headache, Apr. 1997, pp. 256–257.

Nageotte et al., American Journal of Obstetrics and Gynecology, 174/6 (1801–6) (abstract), 1996.

Kymer et al., Journal of Clinical anesthesia, 7/1 (35–9) (abstract), Feb. 1995.

*Primary Examiner*—Phyllis G. Spivack
*Attorney, Agent, or Firm*—Leydig, Voit & Mayer, Ltd.

[57] ABSTRACT

Oral dosage form of droperidol are provided and a method for treating migraine using such oral formulations. The dosage forms include tablets, capsules, powders, effervescent formulations and syrups.

12 Claims, No Drawings

ORAL DROPERIDOL COMPOSITIONS AND METHOD FOR TREATING MIGRAINE

FIELD OF THE INVENTION

This invention relates to the field of migraine treatment.

BACKGROUND OF THE INVENTION

The prevalence of migraine is said to be approximately 6% of the male population and 18% of the female population. Treatment for many patients having the occasional migraine usually involves simple analgesics, non-steroidal anti-inflammatory agents, or specific agents such as ergotamines or triptans. Approximately 10% of migraine sufferers have three or more attacks per month and warrant prophylactic treatment. Preventative agents such as beta-blockers, tricyclic antidepressants and divalproex sodium can reduce but not eliminate migraine attacks in some patients. Thus, there remains a need for migraine specific medications such as sumatriptan. In the remaining population of migraine sufferers, and in those with intolerable side-effects from available drugs, there is a lack of conventional pharmaceutical preparations that exhibit therapeutic effect, without severe side-effects.

Droperidol presently is marketed by Akorn, Inc. under the trademark Inapsine, as an injectable formulation used in anesthesia for preoperative surgery. It has never been approved for use in the treatment or management of migraine attacks.

A limited, uncontrolled, non-blinded, use of droperidol lactate (2.5 mg/ml droperidol) to treat migraine attacks was attempted and the results published in *Headache*, Apr. 1996, p.280. In that publication it was reported that 20 patients received from 2.5 to 7.5 mg droperidol intravenously, in increments of 2.5 mg every 30 minutes until the patient was headache free or until a total of three doses had been administered. All of the patients received prior treatment with migraine therapies. Eighteen of the patients reported to be headache-free by the last dose. Although the article reports on apparently encouraging results in treating migraine attacks with droperidol, no definitive conclusions can be reached from the results reported in that article as the number of patients treated was small, the study was not blinded, all patients received other agents to treat the migraine episode prior to receiving droperidol, and there was no placebo control. Also, there was no attempt to repeat the results with the patients. Further, no attempt was made to prolong therapy beyond the initial treatment to a headache-free state and most patients had continuing symptoms to some degree within 24 hours after the last droperidol treatment.

Additionally, the aforementioned study and article only used intravenous droperidol. Others also have used intramuscular droperidol in uncontrolled studies for treatment of migraine. The use of droperidol by injection raises several issues, not the least of which is inconvenience to the patient, caused by the need to have the droperidol administered by a health care professional.

Accordingly, a need exists for a means to treat patients who suffer from, or are at risk of, a migraine episode, that does not require the use of injections of droperidol.

SUMMARY OF THE INVENTION

In accordance with the present invention, droperidol is supplied in a dosage form that provides better patient tolerance and improved ease of administration. In particular, the present invention relates to the use of oral dosage forms of droperidol.

The dosage forms of the present invention comprise tablets, capsules, powders, syrups and effervescent compositions.

The dosage forms of the present invention may be used to treat migraine episodes, by administration to a patient during a migraine attack, in an amount that is effective to treat symptoms of migraine. The dosage forms of droperidol may be used without pretreatment or in conjunction with other migraine therapies.

The dosage forms of the present invention also may be used to treat patients that are suffering from tension headache, vertigo, or hyperemesis gravidarum. The dosage forms also may be used as antiemetics, to treat nausea and the like, such as that caused by chemotherapy. In each instance the dosage is administered in an amount sufficient to treat the patient's symptoms.

The present invention also provides oral dosage forms of droperidol that comprise from 0.5 to 20 mg of droperidol per unit dosage.

DETAILED DESCRIPTION OF THE PREFERRED EMBODIMENTS

The present invention provides dosage forms of droperidol containing various amounts of droperidol, such as between about 0.5 and 20 mg droperidol per unit dosage, such as tablets and capsules, that are particularly useful. The present invention also provides liquid solutions of droperidol, such as syrups, having a concentration of droperidol from about 0.5 mg to about 20 mg. Powders, in dry form, will contain from about 0.5 mg to about 20 mg droperidol and effervescent compositions which contain from about 0.5 mg to about 20 mg, by weight.

The droperidol may be present as the lactate, or any other suitable organic salts of droperidol may be used, such as tartrate or acetate.

As indicated, patients that are suffering from a migraine episode, tension headache, vertigo, hyperemesis gravidarum, or nausea may be treated. The patients are administered the droperidol, typically in dosages of 2 mg to 20 mg, until the symptoms subside. The maximum dosage of droperidol administered to a patient at a single session usually will be 10 mg, although it may on occasion be as high as 20 mg.

The patients receiving droperidol to treat migraine may be treated with droperidol as a single therapy. By this it is meant that other agents used to treat an active episode of migraine need not be used prior to or in conjunction with the droperidol treatment. Many patients receive various medications for prophylaxis against active migraine episodes, but such prophylactic therapy is not considered to be pretreatment of an active migraine episode, prior to droperidol treatment. Such therapy is nonspecific in that the goal is to prevent or reduce the number of occurrences of active migraine headache, but not the treatment of a specific migraine episode. The present dosage forms will be useful as a first-line treatment of active migraine headache without the prior use of traditional migraine therapy, or as a rescue medication when other treatment has failed.

Presently, an active migraine episode may be treated with any of a number of therapies, including the following: Simple analgesics, such as aspirin or acetaminophen, combination analgesics as with caffeine, vasoconstrictors, narcotics, and the like.

As indicated, the use of droperidol in accordance with the present invention does not require the prior administration of such other agents for treating migraine.

The migraine patients to whom droperidol should be administered are those that are experiencing a migraine episode or are at risk of such an episode. Such patients may be generally described as those meeting the diagnostic criteria for "migraine with aura" or "migraine without aura" as detailed in: "Classification Committee of the International Headache Society. Classification and Diagnostic Criteria For Headache Disorders, Cranial Neuroalgia and Facial Pain", *Cephalgia,* 1988, Vol. 8, Supp. 77 at pp. 19–21; or meeting the diagnostic criteria for "status migrainosus", as detailed therein at pp. 26–27.

For some patients it may be beneficial to administer an additional dose of droperidol after the headache has subsided to reduce the probability that the headache will return in a short period of time. Such an additional dose of droperidol may be used to avoid the use of a sedative or other analgesics within the next few hours after the headache symptoms have subsided. Presently it is typical for patients, after they have been rendered headache-free, to resort to such remedies as sedation or use of analgesics shortly after the headache symptoms have subsided to reduce the recurrence of the migraine symptoms after the patient has become headache-free. The present invention may avoid the need for such remedies.

TABLETS

In order to form in tablets, there are used carriers such as vehicles (e.g. lactose, white sugar, sodium chloride, glucose, urea, starches, calcium carbonate, kaolin, crystalline cellulose, silicic acid, etc.), binders (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. moreover, the tablets may be in the form of a conventional non-coated tablet, or a sugar-coated tablet, gelatin-coated tablet, enteric coated tablet, film coated tablet, or double or multiple layer tablet.

CAPSULES

The capsules may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring.

POWDERS

To form a useful powder, the droperidol may be admixed with at least one inert customary excipient (or carrier) such as sodium citrate of dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acadia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof.

EFFERVESCENT POWDER

Effervescent powder may be formulated by the aid of agents such as sodium bicarbonate, citric acid anhydrous, calcium phosphate monobasic, calcium phosphate dibasic, polyvinylpyrrolidone, polyethylene glycol powder, silica gel, L-Leucine, sodium benzoate, simethicone, mineral oil, isopropyl alcohol, water, flavoring agents, sugar, sorbitol, aspartame, saccharin and coloring agents.

SYRUPS AND SOLUTIONS

Droperidol syrups and solutions may be made by adding ingredients such as water, sugar, fructose, sorbitol, aspartame, saccharin, polyethylene glycol, propylene glycol, alcohol, bentonite, tragacanth, alginates, gelatin, carboxymethylcellulose, methylparaben, propylparaben, sodium benzoate, flavoring agents and coloring agents.

The present invention will be described in terms of the following non-limiting examples.

EXAMPLE 1 TABLET FORMULATION

| INGREDIENT | 0.5 MG/TABLET | 20 MG/TABLET |
| --- | --- | --- |
| Droperidol | 0.5 mg | 20 mg |
| Lactose | 50 mg | 50 mg |
| Corn Starch | 10 mg | 10 mg |
| Magnesium Stearate | 0.5 mg | 1 mg |
| Tablet Weight: | 61 mg | 81 mg |

Tablet Process: The ingredients of 1,000 tablets (61 g for 0.5 mg formulation and 81 g for 20 mg 5 formulation) are blended in a suitable mixer and then are compressed into tablets using standard concave punches. Tablets are packaged into bottles or individual blister strips.

The tablets can be further coated using either aqueous film coating in a suitable coating pan and dried. The coated tablets are packaged into bottles or individual blister strips.

The tablets can be further coated using conventional sugar coating procedure in a suitable coating pan and dried. The tablets are packaged into bottles or individual blister strips.

EXAMPLE 2 CAPSULE FORMULATION

| INGREDIENT | 0.5 MG/CAPSULE | 20 MG/CAPSULE |
| --- | --- | --- |
| Droperidol | 0.5 mg | 20 mg |
| Lactose | 50 mg | 50 mg |
| Polyvinylpyrrolidone | 5 mg | 5 mg |
| Corn Starch | 25 mg | 25 mg |

-continued

| INGREDIENT | 0.5 MG/CAPSULE | 20 MG/CAPSULE |
| --- | --- | --- |
| Magnesium Stearate | 1 mg | 2 mg |
| Capsule Weight | 81.5 mg | 102.0 mg |

Capsule Process: The ingredients are blended for 1,000 capsules (81.5 g for 0.5 mg formulation and 102 g for 20 mg formulation) in a suitable mixer, then filled into hard shell capsules using conventional procedure. The capsules are cleaned and packaged into bottles or individual blister strips.

EXAMPLE 3 POWER FORMULATION

| INGREDIENT | 0.5 MG/BLISTER PACK | 20 MG/BLISTER PACK |
| --- | --- | --- |
| Droperidol | 0.5 mg | 20 mg |
| Sucrose | 50 mg | 50 mg |
| Carboxymethylcellulose | 10 mg | 10 mg |
| Peppermint Spray Dried Flavor | 2 mg | 3 mg |
| Powder Weight: | 62.5 mg | 83 mg |

Powder Process: The ingredients of 1,000 powder units (62.5 g for 0.5 mg formulation and 83 g for 20 mg formulation) are blended in a suitable mixer and filled into individual blister packs.

EXAMPLE 4 EFFERVESCENT TABLET AND POWDER

| INGREDIENT | 0.5 MG/UNIT | 20 MG/UNIT |
| --- | --- | --- |
| Droperidol | 0.5 mg | 20 mg |
| Sodium Bicarbonate | 50 mg | 80 mg |
| Citric Acid Anhydrous | 30 mg | 50 mg |
| Saccharin | 1 mg | 1 mg |
| Silica Gel | 5 mg | 7 mg |
| UNIT WEIGHT | 86.5 mg | 158 mg |

Tablet Process: The ingredients are blended for 1,000 tablets (86.5 g for 0.5 mg formulation and 158 g for 20 mg formulation) in a suitable mixer and compressed into tablets under controlled environmental condition with relative humidity <30%. The tablets are packaged in glass bottles or individually in an aluminum foil pouch to protect from moisture during storage.

Powder Process: The ingredients are blended for 1,000 powder units (86.5 g for 0.5 mg formulation and 158 g for 20 mg formulation) in a suitable mixer in an environmental condition of relative humidity <30%. The individual powder units are packaged in an aluminum foil pouch to protect form moisture during storage.

EXAMPLE 5 SYRUP AND SOLUTION FORMULATION

| INGREDIENT | 0.5 MG/ML | 20 MG/5 ML |
| --- | --- | --- |
| Droperidol | 0.5 mg | 20 mg |
| Lactic Acid qs to pH | 3.5 | 3.5 |
| Sucrose | 50 mg | 250 mg |
| Citrus Flavor | 0.1 mg | 0.5 mg |
| Methylparaben | 1 mg | 5 mg |
| Propylparaben | 0.2 mg | 1 mg |
| Water, qs.ad | 1 ml | 5 ml |
| TOTAL WEIGHT | 1 ml (1 g) | 5 ml (5 g) |

Syrup and Solution Process: In a suitable vessel, droperidol is dissolved with lactic acid with pH adjusted to about 3.5 in sufficient quantity of water. The remaining ingredients are then added and dissolved. Sufficient water is then added for 1,000 units (1,000 ml for 0.5 mg formulation and 5,000 ml for 20 mg formulation). The solution is filtered and filled into bottles.

What is claimed:

1. A method for treating a patient suffering from a migraine episode or tension headache, comprising orally administering droperidol to the patient, in an amount that is effective to treat said symptoms, said amount being from about 0.5 mg to about 20 mg.

2. The method of claim 1 wherein the droperidol is present as a lactate salt.

3. The method of claim 1 wherein the droperidol is present as a tartrate salt.

4. The method of claim 1 wherein the droperidol is present as an acetate salt.

5. The method of claim 1 wherein the droperidol is present in a tablet.

6. The method of claim 1 wherein the droperidol is present in a capsule.

7. The method of claim 1 wherein the droperidol is present in a powder.

8. The method of claim 1 wherein the droperidol is present in an effervescent tablet.

9. The method of claim 1 wherein the droperidol is present in an effervescent powder.

10. The method of claim 1 wherein the droperidol is present in a syrup solution.

11. The method of claim 1 wherein the amount of droperidol is from about 0.5 mg to about 10 mg.

12. The method of claim 1 wherein the amount of droperidol is from about 0.5 mg to about 10 mg.

* * * * *